(12) United States Patent
Tranberg et al.

(10) Patent No.: US 12,702,856 B2
(45) Date of Patent: Aug. 11, 2026

(54) APPARATUS AND METHOD FOR CONTROLLING IMMUNOSTIMULATING LASER THERMOTHERAPY

(71) Applicant: Clinical Laserthermia Systems AB, Lund (SE)

(72) Inventors: Karl-Göran Tranberg, Lund (SE); Stephan Dymling, Lund (SE)

(73) Assignee: Clinical Laserthermia Systems AB, Lund (SE)

( * ) Notice: Subject to any disclaimer, the term of this patent is extended or adjusted under 35 U.S.C. 154(b) by 0 days.

(21) Appl. No.: 18/506,954

(22) Filed: Nov. 10, 2023

(65) Prior Publication Data

US 2024/0082596 A1 Mar. 14, 2024

Related U.S. Application Data

(63) Continuation of application No. 17/185,355, filed on Feb. 25, 2021, now Pat. No. 11,850,442, which is a (Continued)

(30) Foreign Application Priority Data

Apr. 30, 2013 (EP) .................................... 13165962

(51) Int. Cl.
*A61N 5/06* (2006.01)
*A61B 18/00* (2006.01)
(Continued)

(52) U.S. Cl.
CPC .. *A61N 5/0601* (2013.01); *A61B 2018/00023* (2013.01); *A61B 2018/00642* (2013.01); (Continued)

(58) Field of Classification Search
CPC .................. A61N 5/0601; A61N 5/067; A61N 2005/0612; A61N 2005/0626; (Continued)

(56) References Cited

U.S. PATENT DOCUMENTS

| | | |
|---|---|---|
| 5,222,953 A | 6/1993 | Dowlatshahi |
| 6,603,988 B2 | 8/2003 | Dowlatshahi |

(Continued)

FOREIGN PATENT DOCUMENTS

| | | |
|---|---|---|
| CN | 85104234 A | 11/1986 |
| CN | 101325919 A | 12/2008 |

(Continued)

OTHER PUBLICATIONS

China Patent Office, Office Action dated Feb. 26, 2021 with English translation in Chinese Patent Application No. 201811508845.6, 16 pages.

(Continued)

*Primary Examiner* — Aaron F Roane
(74) *Attorney, Agent, or Firm* — Inskeep IP Group, Inc.

(57) ABSTRACT

An apparatus for obtaining an anti-tumour immunologic response by thermotherapy of a treatment lesion covering at least a portion of a tumour is disclosed. The apparatus comprises a heating probe comprising an optical fiber and a cooling catheter. The optical fiber is inserted in the cooling catheter. Further the heating probe has a light emitting area, and the heating probe is interstitially insertable into the tumour of the treatment lesion. The heat probe is internally cooled by a fluid circulating in said catheter. The apparatus further comprises a first thermal sensor member having at least one sensor area. The first thermal sensor member is positionable at a distance from said boundary. The apparatus also comprises a control unit for controlling a power output of said light source based on a measured first temperature.

22 Claims, 9 Drawing Sheets

Related U.S. Application Data continuation of application No. 14/787,754, filed as application No. PCT/EP2014/058934 on Apr. 30, 2014, now Pat. No. 10,960,223.

(60) Provisional application No. 61/817,743, filed on Apr. 30, 2013.

(51) Int. Cl.
*A61B 18/20* (2006.01)
*A61B 18/22* (2006.01)
*A61N 5/067* (2006.01)

(52) U.S. Cl.
CPC ............... *A61B 2018/00678* (2013.01); *A61B 2018/00702* (2013.01); *A61B 2018/00797* (2013.01); *A61B 2018/00898* (2013.01); *A61B 2018/2005* (2013.01); *A61B 2018/20361* (2017.05); *A61B 2018/2261* (2013.01); *A61N 2005/0612* (2013.01); *A61N 2005/0626* (2013.01); *A61N 2005/0627* (2013.01); *A61N 2005/063* (2013.01); *A61N 2005/0659* (2013.01); *A61N 5/067* (2021.08)

(58) Field of Classification Search
CPC ...... A61N 2005/0627; A61N 2005/063; A61N 2005/0659; A61B 2018/20361; A61B 2018/00023; A61B 2018/00642; A61B 2018/00678; A61B 2018/00702; A61B 2018/00797; A61B 2018/00898; A61B 2018/2005; A61B 2018/2261
USPC ........................................................... 607/89
See application file for complete search history.

(56) References Cited

U.S. PATENT DOCUMENTS

2005/0222556 A1 10/2005 Ariura et al.
2009/0198309 A1* 8/2009 Gowda ................ A61N 5/0601 607/102
2013/0066403 A1 3/2013 Giraud et al.
2013/0079852 A1 3/2013 Henriksson et al.
2013/0165915 A1* 6/2013 Thiel ...................... A61B 18/14 606/41
2014/0128881 A1* 5/2014 Tyc .................... A61B 18/1492 606/20

FOREIGN PATENT DOCUMENTS

| | | | |
|---|---|---|---|
| CN | 101972188 | A | 2/2011 |
| EP | 3155995 | A2 | 4/2017 |
| JP | H02182272 | A | 7/1990 |
| JP | 2001046389 | A | 2/2001 |
| JP | 2002102268 | A | 4/2002 |
| JP | 2003297246 | A | 10/2003 |
| JP | 2005287672 | A | 10/2005 |
| JP | 2011516184 | A | 5/2011 |
| WO | WO2007/038415 | A2 | 4/2007 |
| WO | WO2009/124301 | A1 | 10/2009 |

OTHER PUBLICATIONS

China Patent Office, Office Action dated Apr. 14, 2021 in Chinese Patent Application Serial No. 201811509556.8 with English translation, 14 pages.

China National Intellectual Property Administration, Copy of Office Action issued Oct. 23, 2020 in Chinese Patent Application No. 201811509556.8 filed Apr. 30, 2014 (with English translation), 10 pages.

Japan Patent Office, Official Action dated Mar. 13, 2018 in Japanese Patent Application No. JP2016-511079 with English translation, 7 pages.

WIPO, European International Search Authority, International Search Report and Written Opinion mailed Jun. 30, 2014 in International Patent Application No. PCT/EP2014/058934, 10 pages.

* cited by examiner

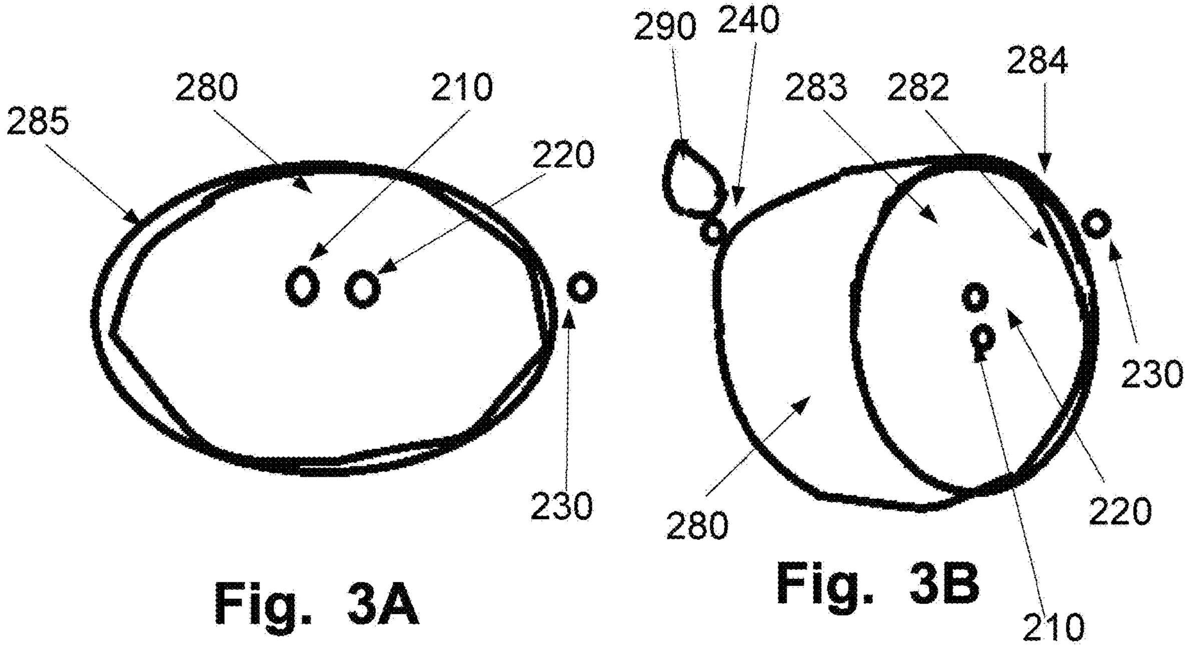
Fig. 3A
Fig. 3B
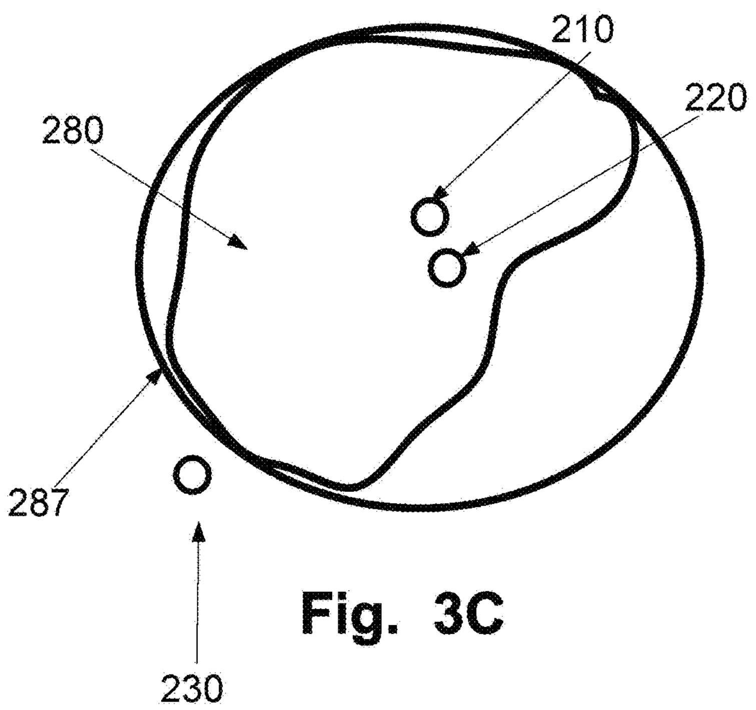
Fig. 3C

APPARATUS AND METHOD FOR CONTROLLING IMMUNOSTIMULATING LASER THERMOTHERAPY

RELATED APPLICATIONS

This application is a continuation of and claims priority to U.S. patent application Ser. No. 17/185,355 filed Feb. 25, 2021, entitled Apparatus And Method For Controlling Immunostimulating Laser Thermotherapy, which is a continuation of and claims priority to U.S. patent application Ser. No. 14/787,754 filed Oct. 28, 2015, entitled Apparatus And Method For Controlling Immunostimulating Laser Thermotherapy (now U.S. Pat. No. 10,960,223 issued Mar. 30, 2021), which is the U.S. National Phase of and claims priority to International Patent Application No. PCT/EP2014/058934, International Filing Date Apr. 30, 2014, entitled Apparatus And Method For Controlling Immunostimulating Laser Thermotherapy, which claims benefit of European Application No. EP13165962.5, filed Apr. 30, 2013 entitled Apparatus And Method For Controlling Immunostimulating Laser Thermotherapy; and U.S. Provisional Application Ser. No. 61/817,743, filed Apr. 30, 2013 entitled Apparatus And Method For Controlling Immunostimulating Laser Thermotherapy; all of which are incorporated herein by reference in their entireties.

FIELD OF THE INVENTION

This invention pertains in general to the field of interstitial thermotherapy of a treatment lesion associated with at least an area of a tumour. More particularly the invention relates a system for controlled heating and destruction of cancer using a heat source. Even more particularly the invention further relates to obtaining an anti-tumour immunologic effect against the treated cancer, i.e. immunostimulating laser thermotherapy.

DESCRIPTION OF THE PRIOR ART

It is known in the art that a tumour may be destroyed by heat, such as thermotherapy. One of the most common thermotherapy techniques is interstitial laser hyperthermia, which destroys tumours by absorption of light. Early experimental and clinical studies used an Nd-YAG laser and bare end fibres inserted into the centre of a tumour. Most of these lacked adequate control of the tissue effect. Methods to improve lesion size included multi-fibre systems, diffuser type fibres and vascular inflow occlusion. However the standard application of interstitial laser hyperthermia results in evaporisation and carbonisation of tissue and relatively unpredictable tissue damage and lesion size.

Studies from rats and humans have shown that heat treatment of cancer may give rise to an anti-tumour immunologic effect. If the dying tumour cells release uncoagulated tumour antigens, these antigens may produce an immune response when presented to the immune system of the host. Thus, the treated tumour will not only be destroyed but the immune effect will destroy remaining tumour, locally or at distant sites, including lymph nodes. The immunologic effect contributes to the selective tissue damage and the relatively small release of growth factors. The low treatment morbidity gives the possibility to use chemotherapy in a more efficient way since chemotherapy can be started before or at the time of local therapy.

Until now there has been no real way of fully controlling and/or optimize this effect. Thus improved control of heat stimulation to obtaining an immunologic effect would be advantageous and may increase patient safety. Further, an improved control may minimise evaporisation and carbonisation of tissue surrounding the heat source and the adverse effects associated therewith.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a apparatus, a method, and a computer-readable medium, for controlling a heat treatment of a tumour for providing an immunologic anti-tumour effect, according to the appended patent claims.

The apparatus and method disclosed herein may be used for controlling tumour destruction and/or for obtaining an anti-tumour effect, such as an immunologic effect. The anti-tumour effect may be a distant effect following local tumour destruction. The anti-tumour effect is triggered by antigens and may destroy any part left of a treated tumour but may also destroy other untreated tumours in the patient. Thus the effect may be seen as a "vaccine" against a tumour. The antigens are a result of a treatment causing cell death but without coagulating/denaturation of tumour antigens. These antigens may be developed over 1 to 5 days after treatment.

According to some aspects of the disclosure, an apparatus for thermotherapy of a predetermined treatment lesion covering at least a portion of a tumour is disclosed. The apparatus comprises a heating probe comprising an optical fiber and a cooling catheter. The optical fiber is inserted in the cooling catheter and the heating probe has a light emitting area. The heating probe is interstitially insertable into the predetermined treatment lesion and is internally coolable by a fluid circulating in the catheter. The apparatus further comprises a light source connectable to the optical fiber for heating the predetermined treatment lesion and at least a first thermal sensor member having at least one sensor area. The first thermal sensor member is positionable at a boundary of the predetermined treatment lesion or at a distance from a boundary of the predetermined treatment lesion to monitor or estimate a first temperature. The apparatus also includes a control unit for controlling a power output of the light source based on the measured first temperature, so that a second temperature at a boundary between the predefined treatment lesion and surrounding tissue is a predetermined temperature.

In some examples of the disclosure of the apparatus, the predetermined temperature at the boundary is in a range of 50 to 55° C. This temperature has shown to improve the anti-tumour effect.

In some examples of the disclosure of the apparatus, the first thermal sensor member is configured to be positionable at a distance 2-7 mm, such as 3 to 6 mm, such as 4 to 5 mm, such as 2 to 5 mm, outside the boundary of the predefined treatment lesion. The control unit is configured to control said power output so that the first temperature is in a range of 44 to 48° C. This temperature range is preferred for avoiding coagulation/denaturation of tumour antigens, hence an anti-tumour effect may be obtained.

In some examples of the disclosure of the apparatus, a second thermal sensor member is positionable at a distance adjacent to the heating probe and the second thermal sensor member is adapted to measure a third temperature and the control unit is used for controlling the power output so that the third temperature is below 200° C.

In some examples of the disclosure of the apparatus, the second thermal sensor member is positionable at a distance less than 5 mm away from the heating probe.

In some examples of the disclosure of the apparatus, the second thermal sensor member is positioned in the heating probe.

In some examples of the disclosure of the apparatus, the first thermal sensor member is configured to be positionable at a distance 2-7 mm inside the treatment lesion to measure the first temperature, the control unit is configured to estimate a temperature at a distance 2-7 mm outside the boundary based on the first temperature.

In some examples of the disclosure of the apparatus, the control unit is configured to control the power output so that the estimated temperature outside of the boundary is in a range of 44 to 48° C.

In some examples of the disclosure of the apparatus, the control unit is configured to estimate the temperature outside of the boundary and/or second temperature by calculations based on a temperature measured by the first thermal sensor member positioned inside the boundary and a temperature gradient.

In some examples of the disclosure of the apparatus, the control unit is adapted to provide a warning if a predefined maximal temperature of the third temperature.

In some examples of the disclosure of the apparatus, the control unit is adapted to provide a warning if a predefined target temperature of the second temperature and/or the a predefined target temperature of the first temperature and/or a predefined target temperature of the estimated temperature outside of the boundary is reached outside a predefined time range.

In some examples of the disclosure of the apparatus, the control unit is configured to inactivate the light source if the predefined maximal temperature and/or the predefined target temperature is reached outside the predefined time range.

In some examples of the disclosure of the apparatus, the predefined time range is between 5 to 15 minutes.

In some examples of the disclosure of the apparatus, at least one guard thermal sensor member is positionable adjacent to an organ at risk.

In some examples of the disclosure of the apparatus, a template is used for positioning and holding the thermal sensor members and the heat probe.

In some examples of the disclosure of the apparatus, the light emitting area is adapted to diffuse the emitted light.

In some examples of the disclosure of the apparatus at least one of the sensor areas of the first and second thermal sensor members is positionable at a depth of the light emitting area of the heat probe.

According to some further aspects of the disclosure, a computer-readable medium having embodied thereon a computer program for processing by a computer, such as the control unit of the apparatus disclosed herein. The computer program comprising a plurality of code segments including obtaining a measured third temperature value by a second thermal sensor member adjacent a heating probe and/or a first temperature from a first thermal sensor member positioned inside or outside a boundary of a predefined treatment lesion further code segments includes controlling, during a warm-up period, a power output of a light source connected to the heating probe being interstitially inserted in the predefined treatment lesion. Other code segments are used for controlling, during a treatment period, the power output such that the third temperature does not exceed a maximal temperature and/or for maintaining the first temperature at a target temperature and/or for maintaining a second temperature at the boarder of the predefined treatment lesion at a target temperature.

In some examples of the disclosure, the computer-readable medium includes a further code segment for providing a warning and/or switching of the power output if the maximal temperature and/or target temperature are reached outside off the warm-up period.

According to some aspects of the disclosure, a method of controlling a tissue heating process is disclosed, including obtaining a measured third temperature value by a second thermal sensor member adjacent a heating probe and/or a first temperature by a first thermal sensor member positioned inside or outside a boundary of a predefined treatment lesion. The method further includes controlling, during a warm-up period, a power output of a light source connected to the heating probe being interstitially inserted in the predefined treatment lesion. The method also includes, controlling, during a treatment period, the power output such that the third temperature does not exceed a maximal temperature and/or for maintaining the first temperature at a target temperature and/or for maintaining a second temperature at the boarder of the predefined treatment lesion at a target temperature.

According some further to aspects of the disclosure, an apparatus for obtaining an anti-tumour immunologic response by thermotherapy of a defined treatment lesion covering at least a portion of a tumour is disclosed. The apparatus comprises; a heating probe comprising an optical fiber and a cooling catheter. The optical fiber is inserted in the cooling catheter. Further, the heating probe has an emitting area, such as an area for emitting light from the fiber to tissue. The heating probe is interstitially insertable into the treatment lesion. The heating probe is, when in use, further internally coolable by a fluid circulating in the catheter.

The term interstitially is defined as inserting a member or probe into tissue, such as into the treatment lesion, the tumour or healthy tissue.

The apparatus further comprises a light source connectable to the optical fiber for heating the treatment lesion. The light source is in use connected to the optical fiber.

Further, the apparatus comprises at least a first thermal sensor member having at least one sensor area. The first thermal sensor member is positionable at a distance adjacent to the heating probe and is adapted to measure a first temperature.

Also, the apparatus comprises a control unit for controlling a power output of the light source based on the measured first temperature so that the first temperature is below 200° C., in operation of the disclosed apparatus, and that a second temperature at a boundary between the treatment lesion and surrounding tissue is between 50 to 55° C.

In some examples of the disclosure, the apparatus comprises a second thermal sensor member having at least one sensor area. The second thermal sensor member is positionable, and in operation positioned at a distance 2-7 mm, such as 3 to 6 mm, such as 4 to 5 mm, such as 2 to 5 mm, outside the treatment lesion, to monitor a third temperature of the surrounding tissue of between 44 to 48° C. The monitored temperature may be used in feedback to control the power output of the probe to keep the temperature stable at the distance outside and/or at the boundary of the treatment lesion. These temperatures are preferred for avoiding coagulation/denaturation of tumour antigens, hence an anti-tumour effect may be obtained.

In some examples of the disclosure, the second thermal sensor member may be positioned 2-7 mm, such as 3 to 6 mm, such as 4 to 5 mm, such as 2 to 5 mm, inside the treatment lesion. By measuring a temperature inside the treatment lesion the second temperature at the boundary between the treatment lesion and surrounding tissue may be estimated by calculation.

In some examples, the third temperature at a distance 2-7 mm, such as 3 to 6 mm, such as 4 to 5 mm, such as 2 to 5 mm outside the treatment lesion may also be calculated by measuring this temperature 2 to 7 mm inside the treatment lesion.

The estimation of the second and/or third temperature may be done by either simulations (e.g. Monte Carlo, finite elements method or ray tracing based on optical properties), estimation of a temperature gradient or other methods readily available for the person skilled in the art.

Additionally and/or alternatively, in some examples, the second thermal sensor member may have multiple sensors spaced apart from each other. By knowing the distance between sensors, the measured temperatures may be used to calculate a thermal gradient.

This way of using a second thermal sensor member having multiple sensors may be viable for some solid tumour where the optical properties are not well established enough to only use the first temperature for estimating the third temperature, but where it is a disadvantage to place the second thermal sensor member outside the treatment lesion where there is a risk that some viable cancer cells are present after performing a treatment. When removing the second temperature sensor member some of the viable cancer cells may be pulled out together with the temperature sensor after the treatment, so called track seeding of cancer cells. The risk of track seeding can be lowered considerably by placing the second thermal sensor member inside the treatment lesion.

The estimated temperatures may be used in feedback to control the power output of the probe to keep the temperature stable at a distance outside of the treatment lesion and/or at the boundary of the treatment lesion. These temperatures are preferred for avoiding coagulation/denaturation of tumour antigens; hence an anti-tumour effect may advantageously be obtained.

In some examples of the disclosure, the first thermal sensor member is positionable at a distance less than 5 mm away, such as 2 mm, such as 3 mm, from the heating probe. At this distance the highest temperature may be reached. Hence it is important to measure and control this temperature so it does not exceed a maximal temperature.

In some examples of the disclosure, the first thermal sensor member is positioned in the heating probe. This may be done to avoid an extra punctuation of the tumour when positioning the first thermal sensor member.

In some examples of the disclosure, the second temperature and/or third temperature may be estimated by calculation based on an estimated temperature gradient and the first temperature. This may be viable for some solid tumour where the optical properties are well established, such as for breast cancer. An alternative is to use a first sensor having more than one sensor element for measuring the gradient to be used when calculating the second temperature. These calculations may be done by the control unit of the apparatus.

Alternatively and/or additionally, the temperature may be estimated using simulations (e.g. Monte Carlo, finite elements method or ray tracing based on optical properties) and the first temperature.

The skilled person will have general knowledge to set-up or program the control unit accordingly after reading the present disclosure.

In some examples of the disclosure, the control unit is adapted to provide a warning if a predefined maximal temperature of the first temperature is reached. Thus patient safety and/or treatment efficiency may advantageously be optimized. Additionally and/or alternatively, in some examples of the disclosure, the control unit is adapted to provide a warning if a predefined target temperature of the second temperature is exceeded. This will allow the practitioner to adjust the parameters for controlling the treatment.

Additionally and/or alternatively, in some examples of the disclosure, the control unit is adapted to provide a warning if a predefined target temperature of the third temperature is exceeded. This will allow the practitioner to adjust the parameters for controlling the treatment.

During a warm-up period, if the maximal temperature or any of the target temperatures are reached outside a predefined defined time range, the control unit may also give a warning. This warning is to indicate that there may be too high absorption close to the probe which needs to be adjusted for or the treatment needs to be aborted. If the second temperature is not obtained within the warm-up period the output power may be too low or the heating probe may need to be moved closer to the boundary of the tumour.

In some examples of the disclosure, the control unit is configured to inactivate the light source if the predefined maximal temperature and/or a predefined target temperature is reached outside the predefined defined time range of the warm up period. Thus the examples automatically protect the patient from carbonization or risks caused by breakage of the heat probe. Additionally, by inactivating the light source if the predefined maximal temperature and/or a predefined target temperature is reached. Coagulation/denaturation of tumour antigens is avoided. The predefined time range may preferably be between 5 to 15 minutes.

Also, during treatment the laser be automatically switched off or blocked if the temperatures are too high. When the temperatures have lowered to a suitable level, the laser may automatically be switched on again.

In some examples of the disclosure, at least a guard thermal sensor member is positionable adjacent to an organ at risk. The temperature measured by the guard thermal sensor member may be used to avoid damage to the sensitive area or the organ at risk.

In some examples of the disclosure, the apparatus comprises a template for positioning and holding the thermal sensor members and the heat probe.

In some examples of the disclosure, the light emitting area is adapted to diffuse the emitted light.

In some examples of the disclosure, at least one of the sensor areas of the first and second thermal sensor members is positionable at the depth of the light emitting area.

According to another aspect of the invention, a computer-readable medium having embodied thereon a computer program for processing by a computer, such as the control unit of the apparatus disclosed herein, is disclosed. The computer program comprises a plurality of code segments.

A code segment is provided for obtaining a measured first temperature value by a first thermal sensor member adjacent a heating probe and/or a temperature from a second thermal sensor member inside or outside a boundary of a treatment lesion.

A code segment is provided for controlling, during a warm-up period, a power output of a light source connected to the heating probe being interstitially inserted in a treatment lesion.

A code segment is provided for controlling, during a treatment period, the power output such that the first temperature does not exceed a maximal temperature and/or for maintaining the second temperature at a target temperature and/or for maintaining a third temperature at a target temperature.

In some examples of the disclosed computer-readable medium, a further code segment is stored thereon for providing a warning and/or switching off the power output if the maximal temperature and/or target temperature are reached before or after the warm-up period.

According to a further aspect of the disclosure, a method of obtaining an anti-tumour immunologic response by thermotherapy of a treatment lesion covering at least a portion of a tumour is disclosed. The method comprises:

controlling a power output of a light source based on a measured first temperature so that the first temperature is below 200° C., when in in operation, and so that a second temperature at a boundary between the treatment lesion and surrounding tissue is between 50 to 55° C.

In some examples of the disclosure, the method comprises heating the portion of the tumour by a heat probe interstitially in the treatment lesion.

In some examples of the disclosure the method comprises measuring a first temperature adjacent the heating probe.

In one example of the disclosed method, the method comprises, measuring a third temperature at a distance 2-7 mm outside the boundary. The third temperature is preferably between 44 to 48° C.

In one example of the disclosed method, measuring a temperature at a distance 2-7 mm inside the boundary; and estimating a third temperature of the surrounding tissue of between 44 to 48° C. is kept at a distance 2-7 mm outside the boundary and/or the second temperature at the boundary based on the measured temperature.

Further embodiments of the invention are defined in the dependent claims, wherein features for the second and subsequent aspects of the invention are as for the first aspect mutatis mutandis.

It should be emphasized that the term “comprises/comprising” when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present invention, reference being made to the accompanying drawings, in which

FIGS. 3A, 3B, 3C, and 3D are schematic illustrations of exemplary treatment lesions and positioning of the heat probe and thermal sensor members;

DETAILED DESCRIPTION

Figure 1:
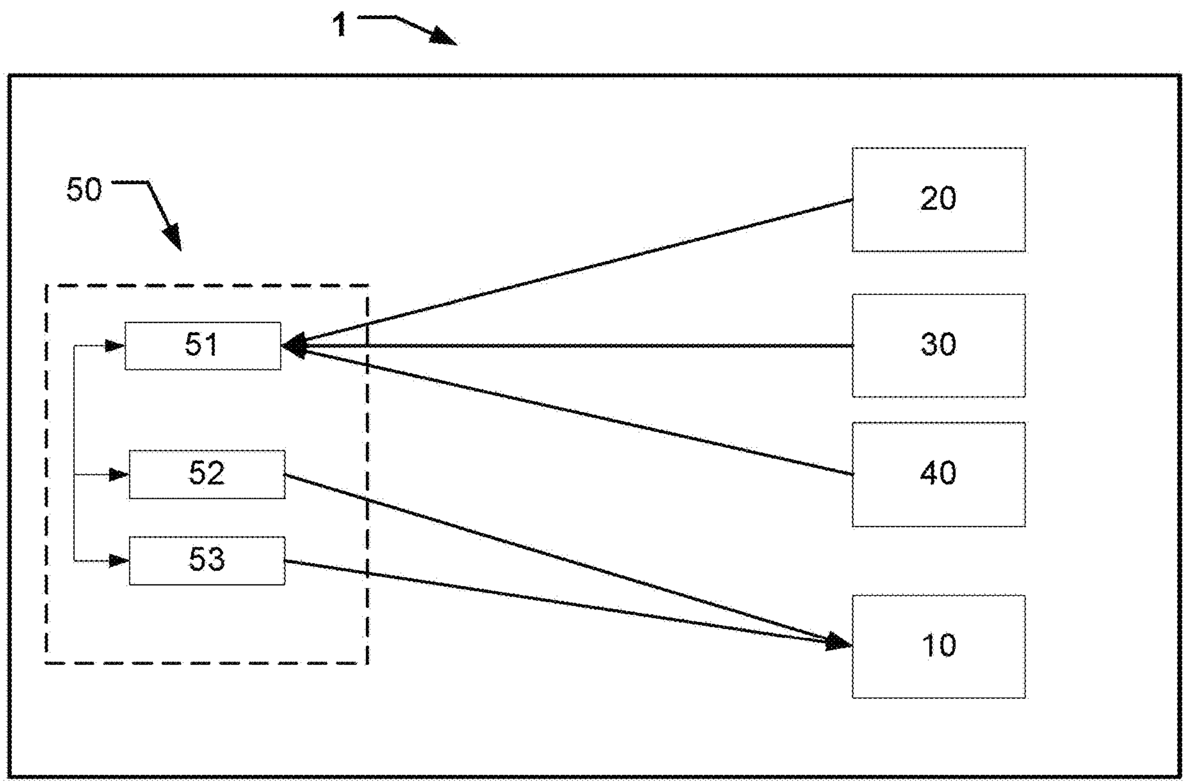
FIG. 1 is a schematic illustration over an exemplary apparatus for obtaining an immune response by thermotherapy of a tumour.

Specific examples of the discloser will be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on examples applicable to an apparatus, method and computer software embodied on a computer for controlling thermotherapy of a treatment lesion covering at least a portion of a tumour. In particular the disclosure relates to an apparatus, method and computer software embodied on a computer for obtaining an anti-tumour immunologic response by thermotherapy of at least a portion of a tumour. However, it will be appreciated that the invention is not limited to this application but may be applied to other areas of thermotherapy treatment of tumours.

In an example according to FIG. 1, a schematic illustration is given over an exemplary apparatus 1 for obtaining an immune response by thermotherapy of a tumour, i.e. an apparatus for immunostimulating laser thermotherapy.

The illustrated apparatus 1 comprises of a main unit 50 having an output unit, such as a display, and an input unit, such as a keyboard, mouse and/or touchscreen (not shown in FIG. 1). The main unit 50 further has a control unit 51 for controlling and adjusting the power output of a heat source, such as a laser generator. The control unit is connected to a pump unit 52 and at least one laser generator 53, such as a laser light source. Alternatively, or in addition, other heat sources may be used, such as RF and microwave sources.

The pump unit 52 and the laser generator 53 are connectable to an interstitially insertable heating probe 10. The heating probe 10 comprises in examples an optical fiber which is inserted into a cooling catheter (not shown in FIG. 1). The cooling catheter is fluidly connected to a pump of pump unit 52 allowing a fluid, such as a cooling liquid, to be circulated in and out of channels of the cooling catheter, thereby cooling the heating probe 10.

The purpose of the internal cooling system is to cool the heating probe to avoid extensive heat at the surface of the heating probe. The risk of char building on the probe which may damage the probe causing it to break is at least advantageously reduced or avoided thanks to the internal cooling system.

Close to the tip of the heating probe 10 is a light emitting area for emitting light from the optical fiber for heating a treatment lesion. Energy, in the example light of a certain power, is emitted from the emitting area of the heating probe 10, in operation thereof, for the heating of the lesion. The probe is preferably in apposition with the treatment lesion, or at least positioned at the treatment lesion. The treatment lesion may cover at least a portion of a tumour to be treated. The covered portion of a tumour has a boundary adjacent healthy tissue surrounding the tumour. Additionally, the heating probe may emit diffused light from the emitting area. The diffused light may be provided by fitting a distal end of the optical fiber with a light diffusor.

In the illustrated example only one heating probe 10 is shown, but depending on the size and shape of the tumour to be treated more than one heating probe may be used.

Additionally to a heating probe 10, the apparatus 1 may include a first thermal sensor member 20, such as a high temperature probe, for measuring the temperature in the proximity to an emitting area of the heating probe 10. The first thermal sensor member 20 is connected to the control unit 51.

Alternatively to positioning the first thermal sensor member 20 outside the heating probe 10, the first thermal sensor member 20 could be positioned in a channel of the heating probe 10. Thereby a separate puncturing location for the thermal sensor member 20 may advantageously be avoided.

The purpose of the first thermal sensor member 20 is to prevent or minimize the risk of carbonization of tumour tissue around the heating probe 10. The term "around" means "adjacent to" and/or "in apposition with". Carbonization may negatively affect treatment of the tumour or damage the heating probe, which should be avoided. Further, carbonization of tissue may increase the risk of adverse effects, such as, bacterial infections or abscess of tissue. Moreover, high temperatures could also damage the material of the heating probe 10 causing the heating probe 10 to break and thereby may cause leakages of the cooling system. The breakage of the heating probe may also lead to depositing of foreign material at the treatment site, with a potential toxic effect. These implications are effectively avoided, at least by the provided first thermal sensor member 20.

Additionally and/or alternatively, under some conditions, the temperature measured by the first thermal sensor member 20 may be used to estimate the temperature of the tissue a defined distance from the treatment lesion or a temperature at a boundary between the at least a portion of the tumour and surrounding healthy tissue. This could be done by obtaining a temperature gradient, e.g. how much the temperature changes per millimeter, by running computer simulations (i.e Monte Carlo, finite elements method or ray tracing based on optical properties). Alternatively and/or additionally, in some examples, a first thermal sensor member having multiple measuring points spaced with a known distance may be used to estimate the thermal gradient.

Additionally and/or alternatively to the first thermal sensor member 20, in some examples, a second thermal sensor member 30, such as a master probe, may be positioned in surrounding tissue, a few millimeters outside a boundary of a defined treatment lesion. Thus, the temperature in the surrounding tissue, outside the portion of the tumour covered by the treatment lesion, may be controlled to obtain an efficient anti-tumour immunologic effect against the treated cancer.

Additionally to the first and/or second thermal sensor member, in some examples, a further thermal sensor member, or a plurality of such thermal sensor members, may be used as a guard thermal sensor member 40. A guard thermal sensor member 40 may be positioned, as a precaution, in close proximity to a sensitive area of an organ to avoid damages due to heat. A sensitive area could be anywhere either inside the treatment lesion or outside of the lesion.

The sensors for measuring the temperature in the first thermal sensor member 20, second thermal sensor member 30 and guard thermal sensor member 40 may, for example, be thermistors, thermocouples or a fiber bragg gratings (FBG).

Alternatively, instead of using punctuating probes for interstitially measuring the temperature, Magnetic resonance imaging (MRI) may be used to measure the temperature while heating the tumour with an interstitially positioned heating probe, such as including a laser source based optical fiber.

Additionally and/or alternatively, in some examples any of the thermal sensor members 20, 30, 40 may have a single measuring point or multiple sensors for measuring at multiple points.

The measured temperatures from the provided sensor members, such as the illustrated thermal sensor members 20, 30, 40, are used as input to the control unit 51 for adjusting the power output of the laser generator 53 by adjusting the power of a laser source thereof, for example by a feedback system.

If the temperature at any of the measure points exceeds a predetermined temperature value, the control unit 51 may decrease the power output of the laser generator 53. Alternatively, the control unit 51 may inactivate the laser generator 53.

If the temperature at any of the measure points becomes less than a predetermined temperature value, the control unit 51 may increase the power output of the laser generator 53. Alternatively, the control unit 51 may activate the laser generator 53, if it previously has been inactivated.

The predetermined temperature may be a single maximum or target value. Alternatively the predetermined temperature may be a range having an upper and a lower threshold temperature.

The adjustment of the output power may be done automatically by the control unit 51. This could for example be done by a control algorithm implemented in the software of the control unit 51. Alternatively and/or additionally, the control unit 51 may provide an alarm, such as to alert a medical practitioner to manually set and/or adjust the power output of the laser generator 53.

A maximal temperature to be set adjacent the heat probe 10, measured by the first thermal sensor member 20, i.e. the high temperature probe, depends on two main properties. Firstly, the material properties of the heat probe 10. The predetermined maximal temperature should be set to a value to prevent the heat probe from breakage. The main issues are that, depending on the material of the cooling probe, the probe may melt or weaken by the heat causing the heat probe 10 to break. Another problem may be that the fluid circulating in the heating probe may vaporize, hence may expand. The internal pressure may then then cause the probe to break. For example, if some plastics are used in the cooling catheter, the temperature should not exceed 170° C., such as 160° C., while some glass material may tolerate to be exposed to much higher temperatures. For the fluid in the cooling catheter, the maximal temperature depends on factors, such as, size of the channels, pump rate, thermal constant of the cooling liquid, maximum power output and the absorption coefficient at the wavelength used by the laser. The maximum output depends not only on the laser generator but is also limited by the size of the emitting area. The emitting area of the heat probe is preferably between 5 to 30 mm in length.

The wavelength may be any wavelength as long as there is a suitable absorption in the irradiated tissue to generate heat. Preferably, the wavelength should have a high penetration close to the heating probe, i.e. low absorption. A too high absorption of energy may increase the delivered heat and temperature very rapidly around the heating probe, thus it may not provide enough energy at the boundary of the at least portion of a tumour covered by the treatment lesion. If not enough energy is provided, the heat generated may not provide the immune response. For example a wavelength with suitable absorption may be found in the visual or near infrared wavelength region, such as in the region of 700 to 1300 nm, such as 900 to 1100 nm such as 1064 nm. Also, as known to the skilled person, scattering of the light will have a role in how the energy is transferred within the tissue.

Secondly, the maximal temperature adjacent the heat probe 10 should be set to a value that lowers risks for the patient but at the same time gives an optimal treatment, such as an optimal anti-tumour immunologic response. The maximal temperature should be set to a value not causing the tissue surrounding the probe to carbonize during the thermotherapy. Also, depending on the total time of the treatment, different temperatures may be required to minimize the risk of carbonization. Other things that may affect the maximal temperatures adjacent the heat probe 10 may be the shape of the tumour, size of the tumour or the defined treatment lesion and/or optical properties of the tissue.

From a medical perspective it is an advantage to limit the maximal temperature in the tissue. The maximum temperature may be reached about 2 to 5 mm away from an emitting area of the cooled heating probe 10. Thus at least one sensor of the first thermal sensor member 20 should preferably be positioned within this distance range, lateral to the middle of the emitting area of the heating probe or in another position close to the emitting area, e.g. close to the tip 316.

Preferably, the maximal temperature adjacent the heating probe 10 measured by the first thermal sensor member 20 should be kept below 200° C. to minimize the risk of carbonization which may cause, for example, bacterial inflammation or abscess in tissue. At the same time, the maximal temperature has to be high enough adjacent the heat probe 10 so that a target temperature at a boundary of the portion of a tumour can be reached. Additionally and/or alternatively the maximal temperature has to be high enough that a target temperature may be obtained at a defined distance from an established boundary of the treatment lesion. This target temperature may be measured by a second thermal sensor member 30.

Preferably a target temperature is between 50 to 55° C. and should be provided at the boundary of the at least a portion of a tumour covered by the treatment lesion to obtain the anti-tumour immunologic response. A too low temperature requires a long treatment time. A longer treatment time may expose the patient to be treated for risks and complications. For most type of tumours the maximal temperature should preferably be above 60° C. to be able to provide the preferred temperature at the boundary. Preferably, the maximal temperature adjacent the heat probe 10 should be below 200° C., such as, 170° C., such as, 160° C., such as 150° C. minimize the carbonization, hence improve the patient's recovery after treatment and reduce the risk of adverse effects, such as risk of inflammations and abscess of tissue. Moreover not exceeding 150° C. also allows most materials to be used in the heating probe 10 without risking breakage due to weakening of the material or vaporization of the cooling fluid. The breakage of the heating probe may also lead to depositing foreign material at the treatment site. Also, some materials may have a potential toxic effect at high temperatures.

Alternatively and/or additionally, the maximal temperature adjacent to the heating probe may be set to a higher or lower temperature depending on if radical or non-radical treatment is wanted. A radical treatment may require a higher temperature to destroy the tumour while a non-radical treatment may require a lower temperature to avoid destroying the tumour or sensitive areas nearby.

Monitoring the temperature either at the boundary of the at least portion of a tumour or at a distance from the boundary of the treatment lesion may be done by a second thermal sensor member 30. The second thermal sensor member 30, e.g. a master probe, may be positioned 2-7 mm, such as between 2 to 5 mm, outside an established boundary of a treatment lesion. The choice of distance is depending on the characteristics of the tumour and the surrounding tissue. The target temperature at the second thermal sensor member 30 may be in the range of 44 to 48° C. for obtaining local radicality and an anti-tumour immunologic response. The preferred temperature at this location is about 46° C. for obtaining an anti-tumour immunologic response.

To obtain the anti-tumour immunologic response and to keep the risk for the patient at a minimum, the target temperatures should be kept stable for a treatment time between 20 to 60 minutes. Preferably the treatment time should be about 30 minutes. Before starting the treatment time, the target temperatures need to be reached. During this warm-up stage the laser output is adjusted until the right temperature is obtained either at the boundary of the at least portion of a tumour or at the second thermal sensor probe 30. The time to target may take between 5 to 15 minutes, such as between 5 to 10 min, depending on the same parameters as previously mentioned, for example, maximum power output and optical coefficients of the different tissues and between different patients.

If the predefined maximal temperature at the first thermal sensor member 20 is reached and exceeded too fast, it may be an indication of bleeding close to the heating probe 10. Bleeding close to the heating probe 10 may require adjustment of the maximal temperature or the treatment may have to be aborted. If the target temperature at the second sensor member 30 is not reached within the warm-up period the maximal temperature at the first thermal sensor member 20 may need to be increased. Alternatively, the treatment may need to be aborted, for example, if the size of the treated lesion has been set too large.

In some examples, when the treatment has been aborted due to a too fast increase of the first temperature adjacent the heating probe 10 or if the second temperature in the surrounding tissue is not reached, the heating probe 10 and the first thermal sensor 20 may be repositioned and the warm-up may be repeated.

Additionally, in some examples when at least one guard thermal sensor member 40 is used to protect at least one sensitive area inside or outside of the treatment lesion, the measured temperature may also be used in the feedback to the control unit 51. Thus the output power may have to be adjusted not to exceed a temperature that may cause damages to the sensitive area. When treating tumours close to the skin surface the guard thermal sensor may be placed on the skin surface to protect the skin from thermal damage.

Figure 2:
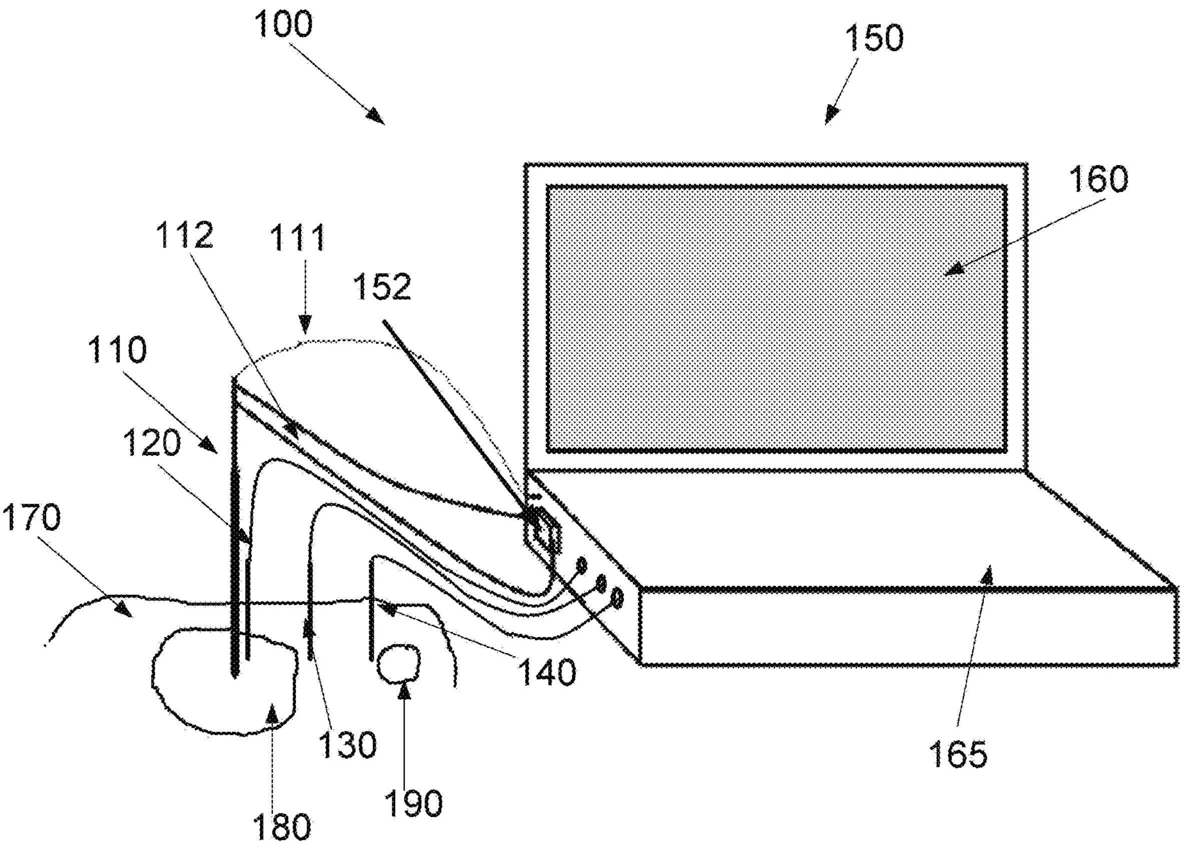
FIG. 2 is a schematic illustration of an exemplary setup of the apparatus.

FIG. 2A is illustrating an example of a setup of an apparatus 100 for obtaining an anti-tumour immunologic response by thermotherapy. The main unit 150 comprises a display 160, an input unit 165, such as a keyboard or a mouse. Alternatively and/or additionally, the display 160 could also be an input unit, such as a touch screen. The main unit 150 further comprises a control unit, not illustrated, a pump unit 152, and a light generator, not illustrated. To the main unit 150 are the heating probe 110 connected via an optical fiber 111. The optical fiber 111 may be connected to the light generator in the main unit 150. Further, the heating probe 110 may be connected with two tubes 112 to the pump unit 152 for pumping and circulating the cooling fluid in the heating probe 110. The heating probe 110 is interstitially insertable into a tumour 180 located in, for example a body organ 170. In the illustrated example, the treatment lesion has the same size as the tumour.

Adjacent the heating probe 110 is a first thermal sensor member 120 positioned. The measured first temperature may be used in a feedback to the control unit 51 for adjusting the power of the laser, both for preventing carbonization of tissue as well as breakage of the heat probe 110. Additionally and/or alternatively the measured first temperature may be used in a feedback to the control unit 51 for adjusting the cooling of the cooling fluid circulating in the heating probe 110.

Additionally and/or alternatively, in some examples may a second thermal sensor member 130 be used for measuring a second temperature in the surrounding tissue outside a boundary of the treatment lesion. The measured second temperature may be used in a feedback to the control unit 51 for adjusting the power of the laser. Additionally and/or alternatively, the measured second temperature may be used in a feedback to the control unit for adjusting the cooling of the cooling fluid circulating in the heating probe 110. The measured second temperature may be used in a feedback to the control unit 51 for adjusting the power of the laser for maintaining the right temperature during the treatment and thereby obtaining the immune response against the treated tumour.

Additionally and/or alternatively, in some organs may a sensitive area 190 that should not be exposed to heat be present in or at a proximity to the tissue being heated. To protect this sensitive area 190, a guard sensor member 140 may be positioned close to the sensitive area 190. The measured temperature at the guard sensor member 140 may be used in a feedback to the control unit for adjusting the power of the laser, hence lowering the temperature at the sensitive area 190.

To aid the practitioner with positioning the heat probe 110 and the first and/or second thermal sensor member 120, 130 a template may be used. The template may be provided after the tumour has been investigated using image guidance, e.g. ultrasound.

FIG. 3A to 3C illustrates different examples of dosimetry planning by establishing a treatment lesion. The dosimetry planning may be varied depending on the tumour size, shape or nearby sensitive organs. For example, may the dosimetry be planned for a radical treatment to destroy the whole tumour at the same time as an anti-tumour immunologic response may be obtained. Alternatively, the treatment may be non-radical where an anti-tumour immunologic response may be obtained in addition to tissue destruction of a part of the tumour. Alternatively, non-radical treatment may only result in an anti-tumour immunologic response without or with minimal tissue destruction.

FIG. 3A is illustrating a cross-sectional view of a tumour 280 having a size allowing that the whole tumour may be covered by the predefined treatment lesion and treated. To be able to treat the whole tumour, the diameter of the tumour may preferably be below 6 cm in diameter, such as below 3 cm in diameter. Thus the treatment lesion 285 may be approximated with the size of the tumour, as illustrated in FIG. 3A. The approximation of the treatment lesion 285 to the boundary of the tumour 280 may be done either as illustrated in FIG. 3A, where a circular or elliptic shaped is fitted to the size of a cross-section of an imaged tumour 280. In this illustration, this fitted shape may approximate the whole boundary of the tumour, thus the whole tumour is covered by the treatment lesion. Alternatively the tumour 280 may be approximated to a 3D volume, such as, a sphere or a three axial ellipsoid. Further alternatives may be to make a fit to the boundary of the tumour using for example polynomials or splines.

Inside the approximated treatment lesion 285 is the heat probe 210 interstitially inserted. Additionally, a first thermal sensor member 220 may be interstitially inserted adjacent to the heat probe. In some examples, additional heat probes may be positioned at different location of the tumour, wherein each having an associated adjacently positioned thermal sensor member. Alternatively, more than one heat probe may be used to heat treat a larger tumour.

Additionally and/or alternatively to the first thermal sensor member 220, a second thermal sensor member 230 may be inserted in the tissue at a distance of between 2 to 7 mm outside of the boundary of the treatment lesion 285.

Alternatively, in some examples when the defined treatment lesion 285 has a boundary identical to the established boundary of the tumour 280, the second thermal sensor member 230 may be inserted in the tissue at a distance of between 2 to 7 mm outside of the boundary of the tumour 280 and the surrounding tissue.

FIG. 3B is a cross sectional view illustrating a tumour 280 where a treatment of the complete tumour may not be suitable, either because the tumour is too large or due to a sensitive area 290 being too close to the tumour 280. In such a case, the predefined treatment lesion may be covering only a portion 283 of the tumour 280. In this case a boundary 284 has to be established where an immunologic-response may be obtained. This may be done either as illustrated in FIG. 3B, wherein a circular or elliptic shaped is fitted with an appropriate size to a cross-section of an imaged tumour. As illustrated, a part of the treatment lesion's boundary 284 overlaps with part of the tumour's boundary 282. To optimize the conditions for providing an immunologic-response effect the tumour's boundary 282 approximated by the treatment lesion's boundary 284 should be as large as possible. Since it is in the interface of the tumours boundary 282 between the portion of a tumour 283, covered by the treatment lesion, and surrounding tissue where the anti-tumour immunologic response effect may be obtained by triggering of antigens.

Alternatively the treatment lesion may be approximated to a 3D volume, such as, a sphere or a three axial ellipsoid. Further alternatives may be to approximate the boundary 284 of the treatment lesion to the boundary 282 of the tumour using for example polynomials or splines.

If the treatment of the complete tumour may not be suitable due to a sensitive area 290 being too close to the tumour 280. The treatment lesion may be chosen sufficiently away from the sensitive area 290, as illustrated in FIG. 3B.

Inside the approximated treatment lesion is the heat probe 210 interstitially inserted. Additionally, a first thermal sensor member 220 may be interstitially inserted adjacent to the heat probe. Alternatively, in some examples, additional heat probes may be used, each having an associated adjacently positioned first thermal sensor member.

Additionally and/or alternatively to the first thermal sensor member 220, a second thermal sensor member 230 may be inserted at a distance of between 2 to 7 mm outside of the treatment lesion's boundary 284.

Alternatively, in some examples when the defined treatment lesion has a boundary 284 identical the established boundary 282 of the tumour portion 283, the second thermal sensor member 230 may be inserted in the tissue at a distance of between 2 to 7 mm outside of the boundary 282 of the tumour portion 283.

A further alternative may be to define more than one treatment lesion to cover a larger part of tumour. Each defined treatment lesion having its own heat probe, adjacent first thermal sensor member and second thermal sensor member associated thereto.

FIG. 3C is illustrating a tumour 280 with an irregular shape. The predefined treatment lesion 287 in this example is defined to cover the whole tumour, such as for a radical treatment. To optimize the conditions for providing an immunologic-response the tumour's established boundary is approximated by the treatment lesion's boundary so that as much as possible to the tumours boundary is overlapping or is adjacent the boundary of the treatment lesion.

Inside the approximated treatment lesion is the heat probe 210 interstitially inserted. Additionally, a first thermal sensor member 220 may be interstitially inserted adjacent to the heat probe. Alternatively, in some examples, additional heat probes may be used each having an associated adjacently positioned first thermal sensor member.

Additionally and/or alternatively to the first thermal sensor member 220, a second thermal sensor member 230 may be inserted at a distance of between 2 to 7 mm outside of the boundary of the treatment lesion 287.

Alternatively, in some examples when the defined treatment lesion 287 has a boundary identical to the established boundary of the portion of the tumour 280, the second thermal sensor member 230 may be inserted in the tissue at a distance of between 2 to 7 mm outside of the boundary of the tumour 280.

A further alternative may be to define more than one treatment lesions to cover a larger part of tumour. Each defined treatment lesion having its own heat probe, adjacent first thermal sensor member and second thermal sensor member associated thereto.

Additionally to the arrangements illustrated in FIGS. 3A to 3C, more than one second thermal sensor member 230 may be inserted at different positions at a distance of between 2 to 7 mm outside of the treatment lesion's boundary and/or the tumour's boundary.

Additionally, in the examples of a sensitive area 290 present close to the tumour or treatment lesion, a guard thermal sensor member 240 may be positioned close to the sensitive area 290.

Figure 3D:
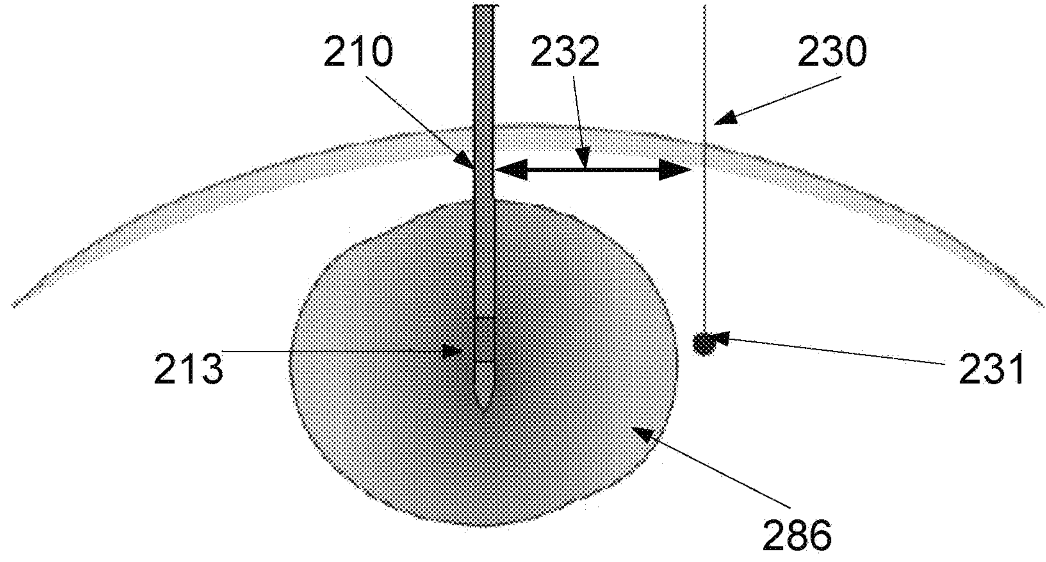

In FIG. 3D is an example of a treatment volume 286 related to a predefined treatment lesion illustrated. The treatment volume 286 may be determined by the distance 232 from the position 231 of a sensor of the second thermal sensor member 230, i.e. a master probe, to an emitting area 213 of a heating probe 210 and the length of the emitting area.

In some examples, only a first thermal sensor member, i.e. a high temperature probe, adjacent the heating probe 210 is used; the treatment volume 286 may be estimated by calculating the location outside the treatment lesion where the temperature is in the range 44-48° C., preferably 46° C. This may be done using simulations or calculations using known optical properties of tissue combined with the measure temperature at the first thermal sensor member. The simulation or calculations may be based on e.g. Monte Carlo, finite elements method or ray tracing. If the first thermal sensor member is equipped with multiple sensors spaced apart, the measured temperatures may be used to calculate a thermal gradient to estimate the location outside the treatment lesion where the temperature is in the range 44-48° C., preferably 46° C.

Alternatively and/or additionally to the examples illustrated in FIGS. 3A to 3D, a second thermal sensor member 230 may be positioned 2-7 mm inside the treatment lesion. By measuring a temperature inside the treatment lesion, the second temperature at the boundary between the treatment lesion and surrounding tissue may be estimated by calculation. Alternatively and/or additionally, in some examples, the third temperature 2-7 mm outside the treatment lesion may also be calculated by measuring this temperature 2 to 7 mm inside the treatment lesion.

The estimation of the second and/or third temperature may be done by either simulations (e.g. Monte Carlo, ray tracing or finite elements method), estimation of a temperature gradient or other methods readily available for the person skilled in the art.

Additionally and or alternatively, in some examples, the second thermal sensor member may have multiple sensors spaced a part the measured temperatures may be used to calculate a thermal gradient.

This way of positioning the second thermal sensor member may be viable for some solid tumour where the optical properties are not well established enough to only use the first temperature for estimating the third temperature, but where it is a disadvantage to place the second thermal sensor member outside the treatment lesion where there is a risk that some viable cancer cells are present after performing a treatment. When removing the second temperature sensor member some of the viable cancer cells may be pulled out together with the temperature sensor after the treatment, so called track seeding of cancer cells. The risk of track seeding may be lowered considerably by placing the second thermal sensor member inside the treatment lesion.

Figures 4A, 4B:
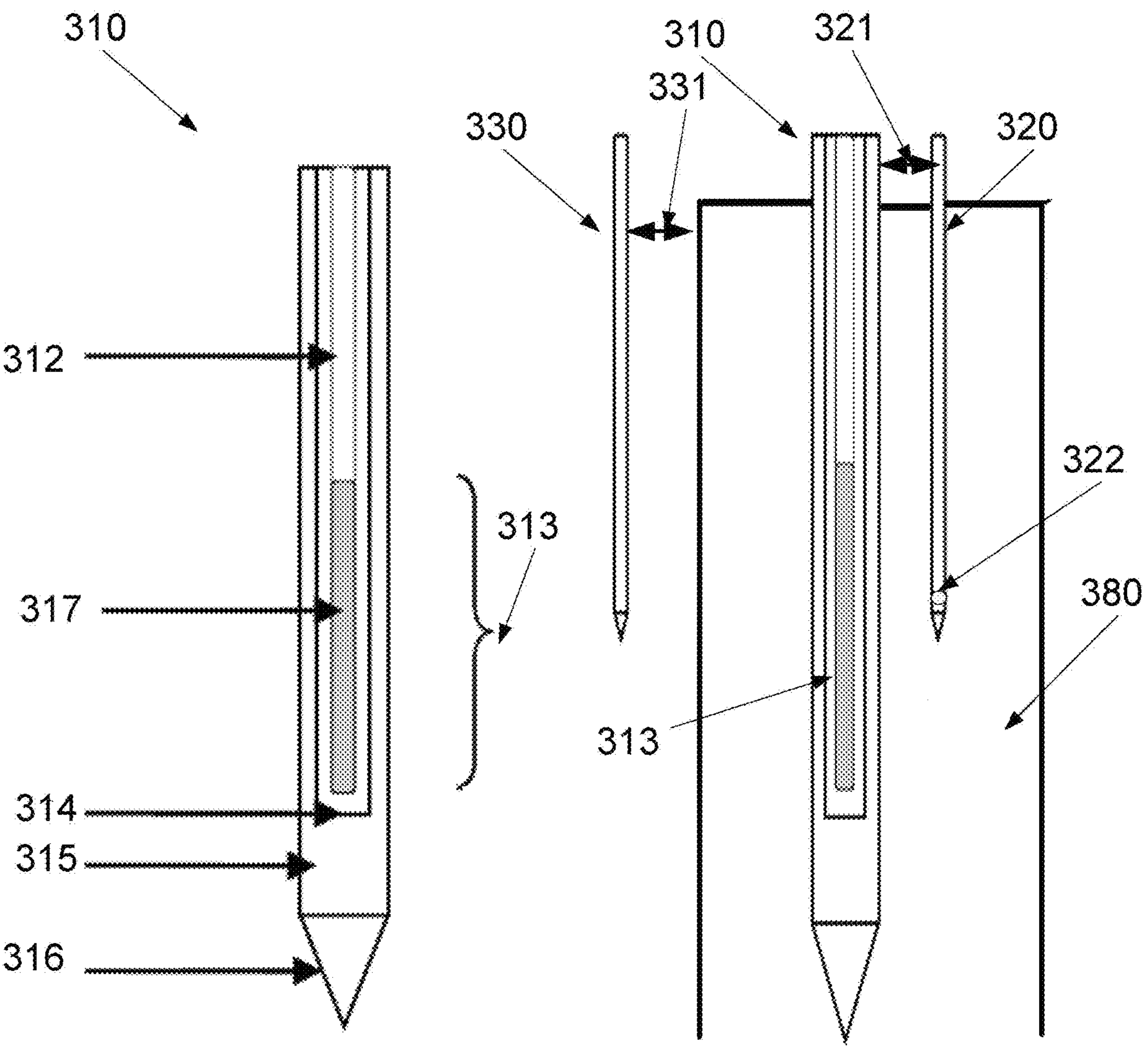
FIGS. 4A and 4B are schematic illustrations of an example of a heat probe and positioning of thermal sensor members in relation to a heat probe.

FIG. 4A is illustrating a distal end of a heating probe 310. The distal end of the heating probe 310 includes an optical fiber 312 centrally positioned in a cooling catheter comprising an inner pipe 314 and an outer pipe 315 in which the cooling fluid is circulated by an external pump. The fiber tip has at least one light emitting area 313. The length of the light emitting area may be between 5 to 30 mm. Additionally, to provide for a more homogenous distribution of the emitted light, the optical fiber 312 may comprise a diffusor 317.

Moreover, the distal en of a heating probe 310 may further comprise a catheter tip 316.

FIG. 4B is illustrating an example of positioning of the distal ends of a heating probe 310, a first thermal sensor member 320 and the second thermal sensor member 330 in a tumour 380 of a treatment lesion. The first thermal sensor member 320 is positioned at a distance 321 away from the heating probe 310. The distance 321 is in the range 2 to 5 mm. Additionally, in some examples, at least one of the sensors 322 of the first thermal sensor member 320 is positioned in the middle of the emitting area 313 of the heating probe 310.

Additionally and/or alternatively, in some examples when a second thermal sensor member 330 is used, the second thermal sensor member 330 should be positioned at a distance 331 of about 2 to 7 mm, preferably between 2 to 5 mm, outside of the estimated boundary of a treated lesion, here illustrated as the boundary of the tumour 380.

Figure 5:
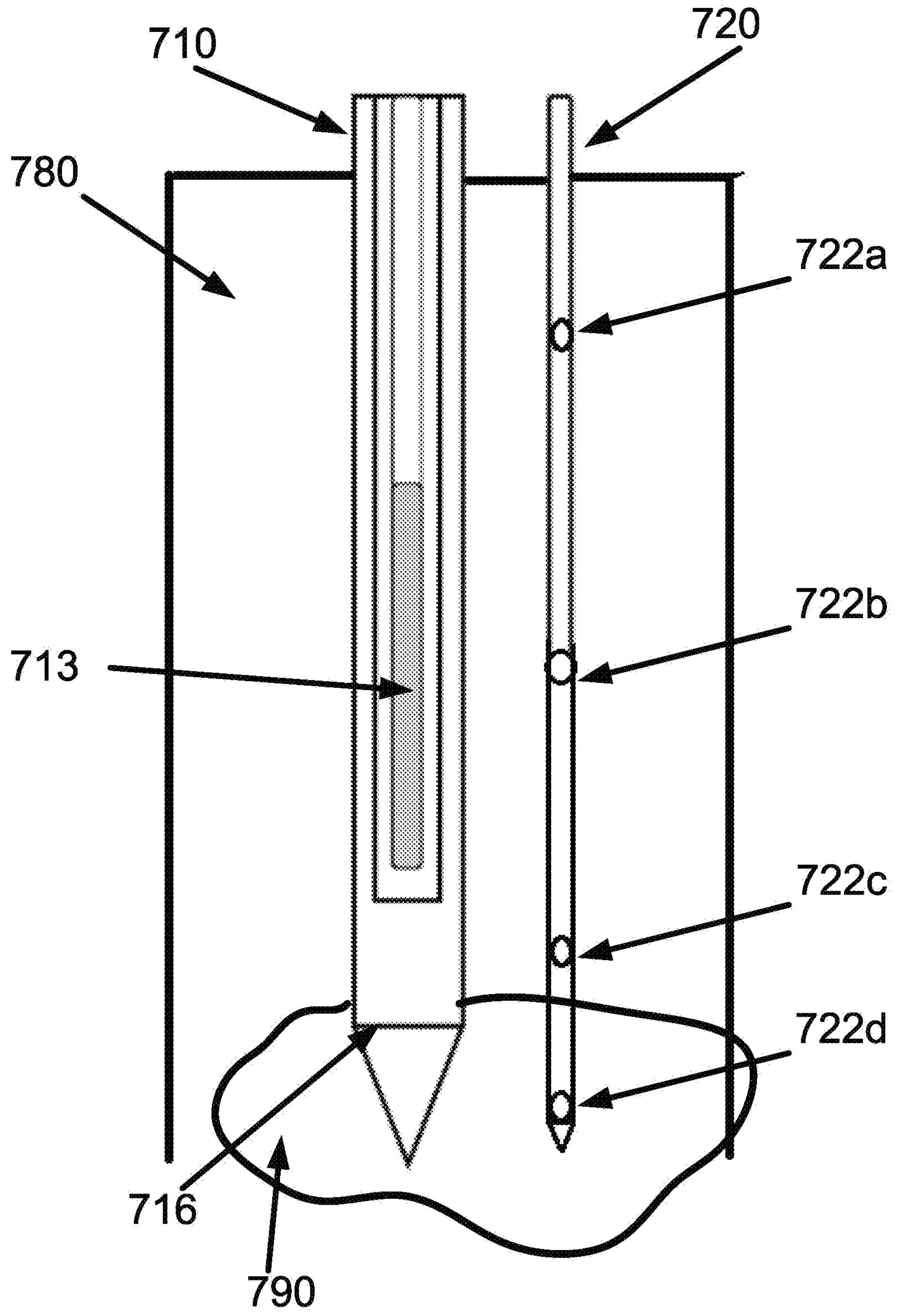
FIG. 5 is a schematic illustration of an example of a multi-sensor thermal sensor member in relation to a heat probe.

In FIG. 5 an example of a first thermal sensor member 720 being a multi-sensor probe is illustrated. The first thermal sensor member is illustrated in the example having four sensors 722*a* to 722*d* at different positions along the length of the interstitially inserted portion of the sensor member. The first thermal sensor 720 is positioned adjacent a heat probe 710 in a tumour 780. In the example, a local bleeding and/or accumulation of blood 790 is illustrated close to the probe tip 716. In most cases, blood has a higher absorption than the tumour. Hence the temperature may increase rapidly to a temperature that may damage the probe or cause adverse effects. By monitoring the temperature close to the tip 716 using the most distal sensor element 722*d*, the power to the laser may be adjusted to avoid excessive heating, if e.g. blood is present. The sensor element may have an associated maximal temperature, such as below 200° C., such as below 170° C., such as below 150° C. at this location. The sensor element 722*b*, lateral to the middle of the emitting area 713 of the heating probe 710, may in some example have a different associated maximal temperature, such as below 140° C., such as below 130° C., such as below 120° C.

Adjusting the maximal temperature of sensor element 772*b* to a new value when detecting an abnormal increase of the heat, which may indicate presence of a bleeding or an accumulation of blood, may decrease the risk of expose the heating probe and the tissue for an excessive heating. This may be obtained thanks to the power output of the laser may be controlled using feedback from more than one thermal sensor element.

By utilizing a multi-sensor probe, such as the first thermal sensor 720, a treatment may be performed during conditions that otherwise may had to be aborted.

Figure 6:
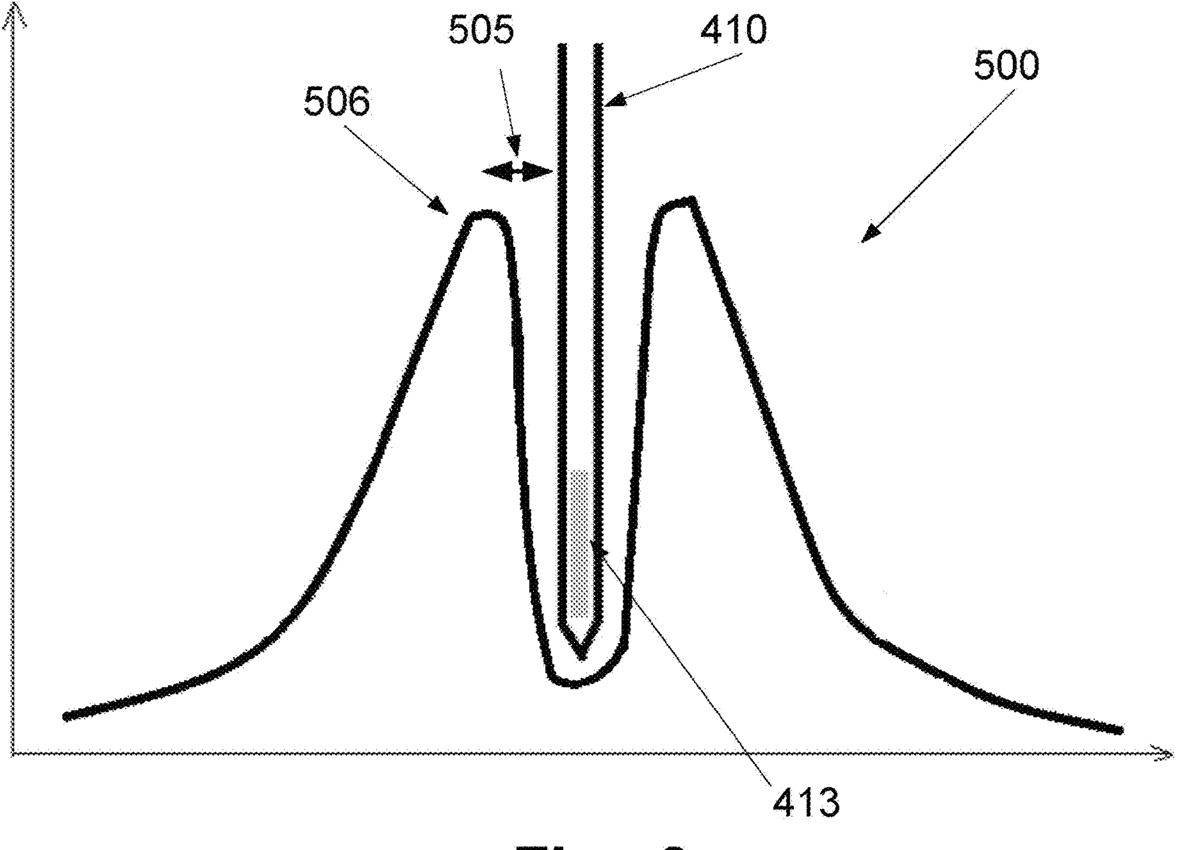
FIG. 6 is a schematic illustration of an example of heat distribution in tissue around a heat probe.

In FIG. 6, an example of a heat profile 500 around an internally cooled heating probe 410 with an emitting area 413 is illustrated. The maximum temperature 506 is approximately measured at a distance 505 between 2 to 5 mm outside of the heating probe 410. Thus the optimal positioning of an adjacent first thermal sensor member is around at proximal to maximal temperature peak 506. Other shapes of the heat profile 500 may be obtained depending on the properties of the heating probe and the optical properties of the tumour.

Figures 7, 8:
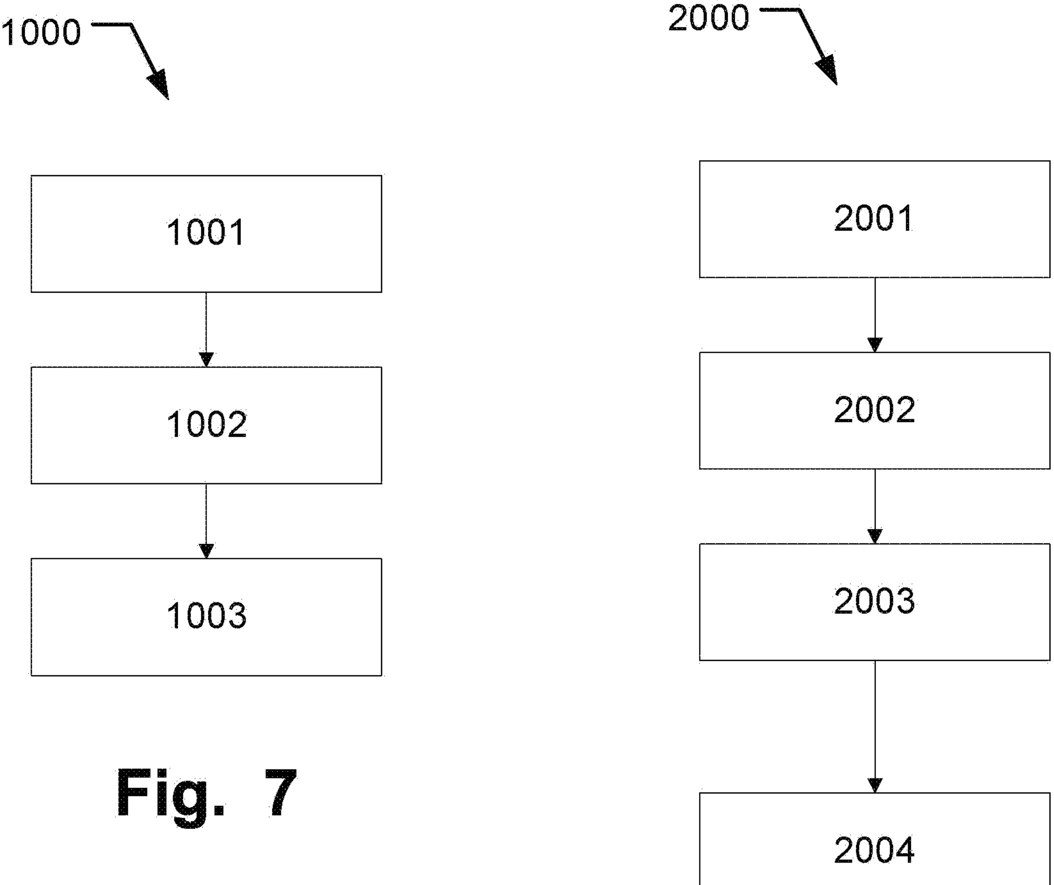
FIG. 7 is a flow chart illustrating a method for controlling an immune response by thermotherapy of a tumour.
FIG. 8 is a flow chart illustrating a method for obtaining an immune response by thermotherapy of a tumour.

FIG. 7 is a flowchart of a method 1000 of controlling an anti-tumour immunologic response by thermotherapy of a treatment lesion covering at least an area portion of a tumour. The steps in the method 1000 may be performed manually or being implemented as code segments in a computer program and executed on a computer or processor, such as the control unit of the apparatus hereinabove disclosed.

The steps of the exemplary method include obtaining a measured first temperature value 1001 by a first thermal sensor member adjacent a heating probe and/or a temperature from a second thermal sensor member inside or outside a boundary of a treatment lesion.

Moreover, the method 1000 includes controlling 1002, during a warm-up period, a power output of a light source connected to the heating probe being interstitially inserted in a treatment lesion. The light source may be that of the afore described examples.

The tissue may be warmed-up during a warm-up period. During this period the power output of a heat source, for example a laser generator connected to the heating probe, may be controlled either manually or automatically until a target temperature is reached. The target temperature may be either the temperature at a boundary of the treatment lesion or at a distance outside the boundary of the treatment lesion, i.e. in the surrounding tissue. This target temperature may be a calculated value based on the accumulated energy provided to the tissue based on temperature measurements adjacent the heating probe.

During the warm-up period of the treatment lesion, care should be taken to avoid that a measured temperatures adjacent the heating probe never exceed a predetermined maximal temperature. This maximal temperature may be set to a value that may lower the risk of carbonization and protecting the probe from breaking due to heat.

One way of performing the warm-up is to increase the output power either continuously or in discrete steps until the target temperature at a position outside of the boundary of the treatment lesion or at the boundary is reached. At the same time the temperature adjacent the heating probe should not exceed its maximal temperature. This feedback may be performed automatically or manually.

Alternatively, another way of performing the warm-up is to decrease the output power from a high output either continuously or in discrete steps until the target temperature at a position outside of the boundary of the treatment lesion or at the boundary is reached. At the same time the temperature adjacent the heating probe should not exceed its maximal temperature. This feedback may be performed automatically or manually.

Subsequent to the warm-up period, or when a treatment lesion is present, the method includes controlling 1003, during a treatment period, the power output such that the first temperature does not exceed a maximal temperature and/or for maintaining the second temperature at a target temperature and/or for maintaining a third temperature at a target temperature.

By monitoring the temperature adjacent the heating probe, that temperature may be prevented to exceed a maximal temperature that may damage or break the probe. It may also prevent carbonization of tissue which may prolong the healing or have adverse effects on a patient being treated.

Additionally and/or alternatively, monitoring the temperature at the boundary of the treatment lesion or at a location a distance outside of the boundary of the tumour or the treatment lesion may increase the success of obtaining an immune response. Since this monitored temperature will be part of the feedback to the apparatus. This may also have an effect on the stability of the required temperature at the boundary of the tumour to obtain the immune response.

Additionally and or alternatively, the temperature at the boundary and/or at a distance outside the boundary may be estimated based on a measured temperature inside the treatment lesion. This measured temperature inside the treatment lesion may either be the temperature from the thermal sensor member positioned adjacent the heat probe but may also be a second thermal sensor member positioned inside the treatment lesion.

It is important during the treatment period to monitor any changes in the measured temperatures so that the temperature adjacent the heating probe does not exceed a maximal value. This may be an indication of a beginning carbonization or abnormal changes of the optical properties. Thus the output power to the laser may need to be adjusted accordingly. Additionally and/or alternatively, sometimes the maximal temperature of the first thermal sensor may need to be adjusted during treatment.

Additionally, it is important that the temperature at a boundary of the treatment lesion or outside of a boundary of the treatment lesion is maintained at the right level to increase the likelihood of an optimised immune response against the tumour. Additionally, in some examples, the boundary of the treatment lesion is defined as the estimated boundary of the tumour portion covered by the treatment lesion.

Additionally, in some examples, the method includes providing a warning and/or switching of the power output if the maximal temperature and/or target temperature are reached outside of the warm-up period.

If the temperature adjacent the heating probe increases too rapidly, such as exceed the set maximal temperature. This may indicate local bleeding or accumulation of blood around the heating probe and/or first thermal sensor member. Bleeding may cause problems due to the high absorption and the treatment may need to be aborted due to risks of damaging the heating probe or risk of adverse effects to the patient.

Additionally, if the target temperature at a boundary of the treatment lesion or outside at a distance from a boundary of the treatment lesion is not reach during the expected time, this may indicate that the output is too low and/or that the target temperature adjacent the heating probe is set to be too low. This may be due to variations of the optical properties between patients. Either the target temperature next to the heating probe may need to be increased and/or the output power to the laser needs to be adjusted.

An alternative is to repositioning the heating probe closer to a boundary of the treatment lesion.

Also, in case the temperature at or outside of the boundary of the tumour would fall below their target temperatures, the control unit may give a warning and/or automatically temporary pause a treatment timer. The timer may either manually and/or automatically start again when the right temperature is obtained. Thus, the treatment period may last for an effective time.

FIG. 8. is a flowchart over a method 2000 of obtaining an anti-tumour immunologic response by thermotherapy of a treatment lesion covering at least an area portion of a tumour. Firstly the tumour and the surrounding tissue have to be investigated to establish size and shape of the tumour. Thus may be done using ultrasound, MRI or other suitable imaging modalities.

The method includes controlling 2001 a power output of a light source based on measured temperatures so that a first temperature adjacent the light source is below 200° C., in operation, and so that a second temperature at a boundary between the treatment lesion and surrounding tissue is between 50 to 55° C.

Additionally and/or alternatively, the method may include positioning 2002 a heat probe interstitially in the treatment lesion for heating the portion of the tumour covered by the treatment lesion.

Additionally and/or alternatively, the method may include positioning 2003 a first thermal sensor member adjacent the heating probe for measuring a first temperature. Additionally and/or alternatively, the step 2002 may include positioning a second thermal sensor member at a distance 2-7 mm outside the boundary for monitoring a third temperature of the surrounding tissue between 44 to 48° C. Additionally and/or alternatively, the step 2002 may include positioning a second thermal sensor member at a distance 2-7 mm inside the boundary for measuring a temperature. If the second probe is positioned inside the treatment lesion, such as inside the portion of the tumour covered but the treatment lesion the third temperature used for estimating a third temperature of the surrounding tissue of between 44 to 48° C. at a distance 2-7 mm outside the boundary and/or the second temperature of 50 to 55° C. at the boundary.

Additionally and/or alternatively, the method may include controlling steps of controlling 2003, during a warm-up period, the power output of a light source connected to the heating probe. Additionally the controlling step may include controlling, during a treatment period, the power output such that the first temperature does not exceed a maximal temperature and/or for maintaining the second temperature at a target temperature.

Additionally if at least a second thermal sensor member is used, the controlling step may includes controlling 2003, during a warm-up period, the power output of a light source connected to the heating probe. The step also includes controlling, during a treatment period, the power output such that the first temperature does not exceed a maximal temperature and/or for maintaining the second temperature at a target temperature and/or for maintaining a third temperature at a target temperature.

Additionally and/or alternatively, the method may include the providing 2004 a warning and/or switching of the power output if the maximal temperature and/or target temperatures are reached before or after the warm-up period.

During the warm-up period and the treatment period, the heating may be done using a continuous light source or a pulsed light source. Alternatively, both continuous light and pulsed light may be used, such as continuous light during the warm-up and pulsed light during the treatment period.

Additionally, in some examples, if during the treatment period the monitored or estimated temperature at the boundary or outside of the boundary of the tumour would fall below a target temperature, the control unit may give a warning and/or automatically temporary pause a treatment timer. The timer may either manually and/or automatically start again when the right temperature is obtained. Thus the treatment period may last for an effective time.

Additionally, the method may further include measuring a temperature using a guard thermal sensor member positioned adjacent a sensitive area of an organ as herein above disclosed in relation to the apparatus.

Example

An experimental example was performed in vitro to demonstrate that the cooling catheter of the heat probe is able to handle the required laser levels of a full treatment interval without damage. Also it was demonstrated that a feedback system for detecting the temperature close to the catheter and adjusts the power according to this temperature may be used to prevent carbonization which may lead to catheter breakdown or adverse effects for the treated patient.

The test was done with minced bovine muscle heated to 37° C. in a water bath. A heating probe, a first thermal sensor member positioned 2 mm from the heating probe and a second thermal sensor member positioned 20 mm from the heating probe was inserted in the minced muscle. The cooling catheter of the heating probe was filled with water at room temperature and pumped at a flow rate of 20 ml/minute. To really push it, the power effect was set almost to max already from the beginning and then lowered. The testing conditions were regarded to be extreme and were applied in order to stress the system.

A feedback control was implemented so when the target temperature of 46° C. was reached at the second thermal sensor member, laser thermo-therapy was delivered for 30 min. When the temperature at the second thermal sensor member exceeded 46° C., the laser was turned off; when it dropped below 46° C., the laser was turned on (on/off regulation). Also, when the temperature exceeded 150° C. at the first thermal sensor member, the laser emission power was lowered by steps of 1W until the monitored temperature dropped below 150° C. The regulation was performed both during the warm-up interval and during the treatment, if necessary.

The treatment session was concluded by a cooling down period of 5 minutes.

Figure 9:
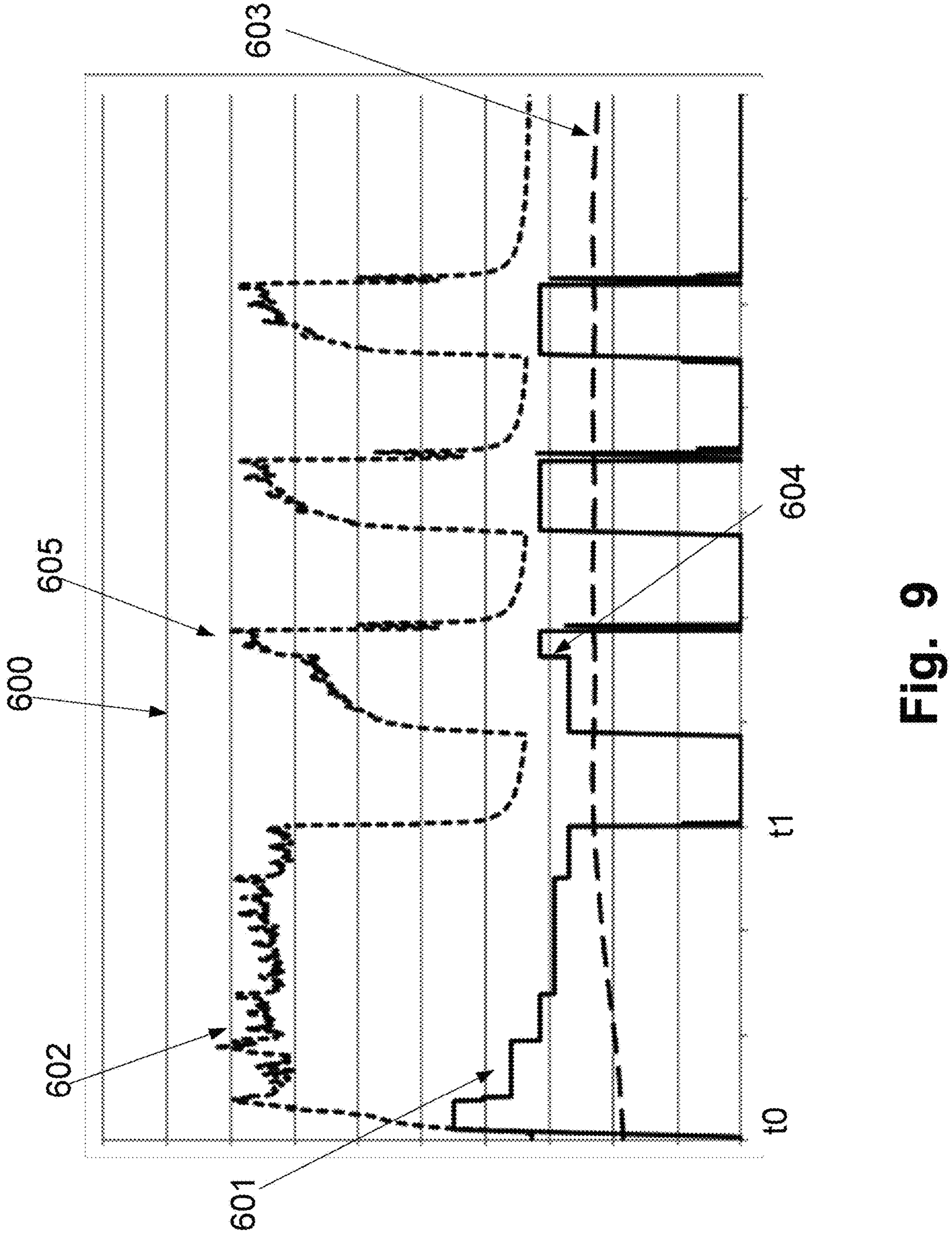
FIG. 9 is a graph illustrating an example of a relation between laser output and heat next to a heat probe and outside the treatment lesion.

FIG. 9 is showing a graph 600 of a result of one test carried out. The solid line 601 shows the power output, the upper dashed line 602 shows the measured temperature of the first thermal sensor member and the lower dashed line 603 shows the measured temperature of the second thermal sensor member. When the measured temperature of the second thermal sensor member reached the target temperature of 46° C. at time t1 the warm-up period ended and the treatment period started. Between t0 and t1 the output was adjusted down each time the temperature of the first thermal sensor member exceeded 150° C. As clearly visible from the graph 600 is that when the power output was adjusted down, the temperature initially decreased and then started to increase. After time t1, when the treatment interval started, the power output of the laser was regulated to maintain a stable temperature of 46° C. at the second thermal sensor member, i.e. the master probe. Even during the treatment interval the output may needs to be adjusted. For example, peak 604 is an increment in the power output was almost immediately results in an increment in the temperature adjacent the heating probe, peak 605.

The inspections on the meat sample and on the catheter tip show that damage of the heating probe may be avoided by adjusting the power so as to obtain a maximum temperature at the position of the first thermal sensor member.

It resulted from the similar tests shows that the time necessary to reach the maximum temperature of 150° C. may vary significantly depending on the optical properties of the tissue, mainly due to its blood content. In fact, the temperature of 150° C. has been reached after only few seconds during the warm-up when a darker sample was used. The heat diffusion seemed to have a different behavior in respect of the one obtained treating lighter samples, the tendency is to have a slower response of the temperature detected by the second thermal sensor member, i.e. master probe. Therefore this temperature tends to raise few degrees over 46° C. at the beginning of the treatment time. One explanation could be the stronger absorption close to the diffused heating probe causes an overshoot of energy that is diffused to the boundary of the treated tumour after the warm-up time. This aspect needs to be investigated in vivo since the blood perfusion may significantly affect this phenomenon.

From the coloring of the lesion it is possible to observe that the maximum temperature is reached at a distance of about 2 mm from the central axis of the diffused fiber tip due to the cooling system. This indicates that the positioning of the first thermal sensor member, i.e. high temperature probe, at a distance of 2 mm from the central axis of the heating probe is correct to detect the highest temperature reached in the tissue, given that the latter is approximately homogeneous The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The indefinite articles “a” and “an,” as used herein in the specification and in the claims, unless clearly indicated to the contrary, should be understood to mean “at least one.” The phrase “and/or,” as used herein in the specification and in the claims, should be understood to mean “either or both” of the elements so conjoined, i.e., elements that are conjunctively present in some cases and disjunctively present in other cases.

What is claimed is:

1. A computer-readable medium having embodied thereon a computer program for processing by a computer, the computer program is for thermotherapy of a predetermined treatment lesion covering at least a portion of a treatment lesion, and wherein said computer program comprising a plurality of code segments for:

obtaining at least one image of said treatment lesion and a laser-based heating probe arranged in said treatment lesion;

obtaining a first temperature of a first temperature area defined inside a boundary of said treatment lesion and adjacent to said laser-based heating probe, wherein said first temperature area is provided from a Magnetic Resonance Imaging (MRI);

monitoring, during a treatment period, said first temperature and switching off said laser-based heating probe, and/or providing a warning, should said first temperature exceed a defined maximal temperature.

2. The computer readable medium according to claim 1, comprising a code segment for obtaining a second temperature from said Magnetic Resonance Imaging (MRI) of a second temperature area defined outside of or at said boundary of said treatment lesion.

3. The computer readable medium according to claim 2, comprising a code segment for maintaining said second temperature at a target temperature by controlling a power to said laser-based heating probe, wherein predefined treatment lesion is obtained.

4. The computer-readable medium according to claim 3, comprises a code segment for providing a warning and/or switching of said laser-based heating probe if said target temperature is exceeded.

5. The computer-readable medium according to claim 3, wherein said controlling of said power to said laser-based heating is performed using a feedback control.

6. The computer-readable medium according to claim 3, wherein said target temperature is set to a range between 44 to 55° C.

7. The computer-readable medium according to claim 6, wherein said target temperature is set to provide an anti-treatment lesion immunologic response.

8. The computer-readable medium according to claim 2, wherein said second temperature area is arranged 2 to 7 mm outside said boundary of said treatment lesion.

9. The computer readable medium according to claim 2, wherein said second temperature is used for minimizing unpredictable tissue damage and lesion size to minimizing damage to healthy tissue.

10. The computer-readable medium according to claim 1, wherein a maximum temperature is set to a temperature below 120° C.

11. The computer readable medium according to claim 1, comprising a code segment for obtaining a third temperature from said Magnetic Resonance Imaging (MRI) of a third temperature area defined in adjacent to an organ at risk.

12. The computer-readable medium according to claim 11, comprises a code segment for providing a warning and/or switching of said laser-based heating probe if a maximum temperature of said third temperature is exceeded.

13. The computer readable medium according to claim 11, comprising a code segment wherein said third temperature is used in a feedback control to control said third temperature by adjusting said power of said laser-based heating probe to protect said organ at risk.

14. The computer-readable medium according to claim 1, wherein said laser-based heating probe has a diffusor arranged in said treatment lesion.

15. The computer readable medium according to claim 14, wherein said diffuser has a length between 5 to 30 mm.

16. The computer-readable medium according to claim 1, comprising a code segment for performing an initial warm-up period.

17. The computer readable medium according to claim 1, wherein said treatment lesion has the same size as a tumour to be treated.

18. The computer readable medium according to claim 1, comprising a code segment to run a treatment for a pre-defined period of time.

19. The computer readable medium according to claim 1, wherein said laser-based heating probe uses a wavelength with an absorption wavelength in visual or near infrared wavelength region.

20. The computer readable medium according to claim 19, wherein said wavelength region is 700 to 1300 nm.

21. The computer readable medium according to claim 1, wherein said first temperature is used for minimizing evaporisation and carbonization of tissue in said treatment lesion.

22. The computer readable medium according to claim 1, wherein said first temperature is used for minimising unpredictable tissue damage.

* * * * *